United States Patent [19]
Dam

[11] Patent Number: 5,880,364
[45] Date of Patent: Mar. 9, 1999

[54] NON-CONTACT ULTRASONIC MICROMEASUREMENT SYSTEM

[75] Inventor: Naim Dam, Muttontown, N.Y.

[73] Assignee: Cosense, Inc., Hauppauge, N.Y.

[21] Appl. No.: 961,607

[22] Filed: Oct. 31, 1997

[51] Int. Cl.$^6$ ................................................. G01F 23/28
[52] U.S. Cl. ................................. 73/149; 73/290 V
[58] Field of Search .................... 73/864.23, 864.24, 73/290 V, 149; 364/479.01

[56] References Cited

U.S. PATENT DOCUMENTS

| | | | |
|---|---|---|---|
| 3,237,451 | 3/1966 | Haef | 73/149 |
| 4,221,004 | 9/1980 | Combs et al. | 73/290 V |
| 4,437,497 | 3/1984 | Enander | 141/1 |
| 4,448,207 | 5/1984 | Parrish | 73/290 V |
| 4,572,253 | 2/1986 | Farmer et al. | 73/290 V |
| 4,658,834 | 4/1987 | Blankenship et al. | 73/290 V |
| 4,675,854 | 6/1987 | Lau | 367/908 |
| 4,715,226 | 12/1987 | Dorr | 73/290 V |
| 4,818,492 | 4/1989 | Shimizu | 73/864.24 |
| 4,864,856 | 9/1989 | Ichikawa et al. | 73/864.25 |
| 4,883,100 | 11/1989 | Stembridge | 141/1 |
| 5,109,347 | 4/1992 | Quick, Jr. et al. | 364/479 |
| 5,127,266 | 7/1992 | Maresca, Jr. et al. | 73/290 V |
| 5,184,512 | 2/1993 | Hrdlicka et al. | 73/584 |
| 5,263,371 | 11/1993 | Maresca, Jr. et al. | 73/290 V |
| 5,303,585 | 4/1994 | Lichte | 73/290 V |
| 5,465,629 | 11/1995 | Waylett, Jr. | 73/864.24 |
| 5,670,710 | 9/1997 | Atkinson | 73/61.45 |
| 5,705,750 | 1/1998 | Mizukami et al. | 73/864.24 |

*Primary Examiner*—Ronald Biegel
*Attorney, Agent, or Firm*—Gordon D. Coplein

[57] ABSTRACT

A non-contact ultrasonic system for measuring the volume of liquid in a container in which an ultrasonic sensor is disposed opposite the top of the container. A circuit provides pulses of ultrasonic energy for transmission through the air to the air-liquid interface of liquid in the container and for measuring the round trip transit time from the sensor to the interface and back to the sensor. A computer is programmed with dimensional data of the container internal volume and computes the volume of liquid in the container based on the dimensional data and the round trip transit time. The computed volume data is stored. The system can measure the volume of a plurality of containers using a plurality of sensors that are operated in sequence or at the same time or single sensor in which the plurality of sensors are moved relative to the single sensor for the volume of each of the sensors to be sequentially measured.

20 Claims, 4 Drawing Sheets

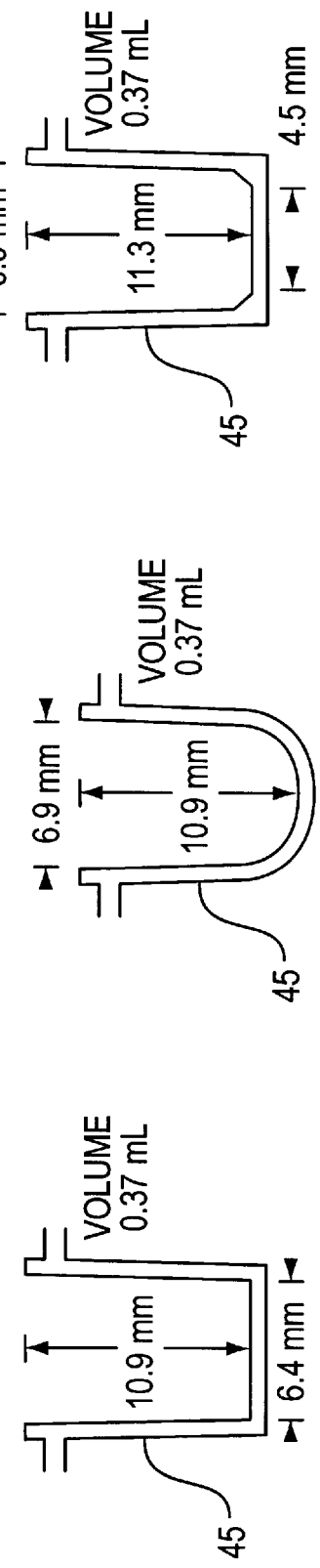

NON-CONTACT ULTRASONIC MICROMEASUREMENT SYSTEM

BACKGROUND OF THE INVENTION

The automated handling of large numbers of liquid samples is necessary in many pharmaceutical and chemical applications, such as drug packaging and testing of various types of liquids including blood reagents and laboratory assays. In such applications, the volume of the liquid in a large number of sample containers must be measured accurately on a high-speed basis. The samples are often of micro-liter size in test tubes or vials having restricted size openings.

In a manual, or semi-automated filling process, the liquid is aspirated into the containers using a pipetting technique and a measurement is made of the liquid level by inserting a probe into the container until it contacts the liquid. This is highly undesirable, particularly when the samples are contaminated, contain toxic liquids, or the sterility of the newly packaged product is to be preserved. Also, the step of making the measurement is relatively slow and sometimes produces inaccuracies.

BRIEF DESCRIPTION OF THE INVENTION

The present invention is directed to a non-contact ultrasonic liquid level measuring system for products that are dispensed into containers such as tubes, vials, etc. The system can operate on a single channel basis sequentially or on a multi-channel basis to measure sequentially or in parallel the amount of fill of a plurality of such containers.

In accordance with the invention, a narrow beam of ultrasonic energy is transmitted from a sensor to the open top of an opposing container to be reflected from the air-liquid interface of the container back to the sensor. The round trip transit time of the energy is calculated. The height and inner diameter parameters of the containers being measured are previously stored and a microprocessor uses this data and the measured round trip time to calculate the volume of liquid in the container. All of this is done without contact of any type with the liquid.

The system can measure containers on an individual basis and there can be a single sensor below which a series of containers held in a tray are passed one at a time. The measured volume data of all of the containers is stored to produce a data map of the measurements. In a preferred embodiment, there is a bank, or row, of a plurality of the sensors that oppose a corresponding row of a plurality of containers. The sensors of the row are actuated and a calculation is made of the liquid volume in each container of the row. The plurality of sensors sensors of the bank are operated sequentially or in parallel and the calculated volume result is stored. In this manner, the volume data for the containers in each row is mapped and has a signature.

OBJECTS OF THE INVENTION

It is therefore an object of the present invention to provide a novel system for filling containers using non-contact ultrasonic liquid level measurement.

Another object is to provide a system for filling containers using non-contact ultrasonic liquid level measurement in which the liquid level of a plurality of such containers is measured sequentially or at the same time.

A further object is to provide a system for measuring the volume of the liquid in each of a plurality of containers and producing a map of the results.

Still another object is to provide a system for measuring the volume of the liquid in each of a plurality of containers having different internal volumes without physical contact of the liquid.

An additional object is to provide a non-contact ultrasonic system for measuring the volume of liquid in each of a plurality of containers and producing a map of the results.

BRIEF DESCRIPTION OF THE INVENTION

Other objects and advantages of the present invention will become more apparent upon reference to the following specification and annexed drawings in which:

FIGS. 4A, 4B and 4C are views of different forms of containers; and

DETAILED DESCRIPTION OF THE INVENTION

Figure 1:
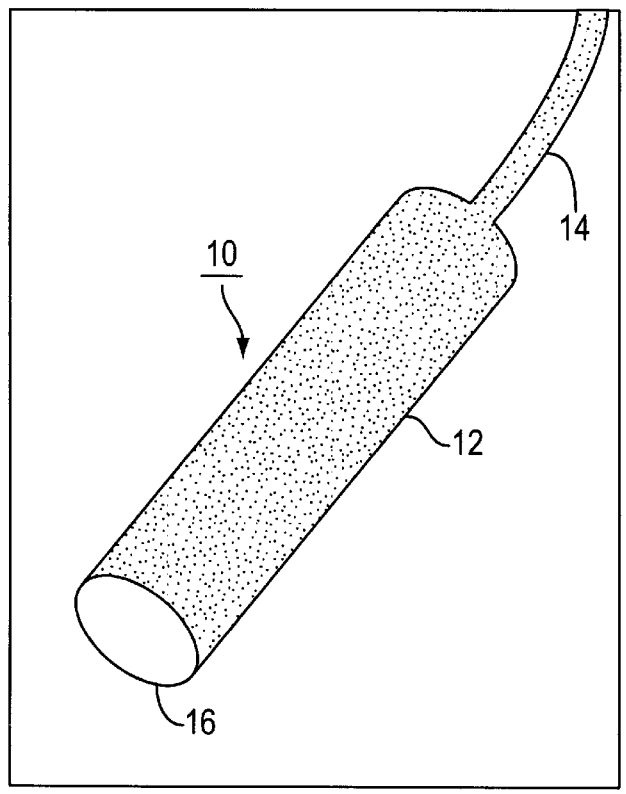
FIG. 1 is a diagram of a typical transducer utilized with the invention.

FIG. 1 shows an ultrasonic sensor 10 that is useful with the invention. The sensor has a generally cylindrical body 12 of any suitable material compatible with the environment under which the measuring process is being carried out. A lead 14 enters one end of the body 12 and carries the necessary wires to supply operating signals to a transducer element at the other end 16 of the body. The transducer element typically is of the piezoelectric type, for example, PZT material. Typical dimensions for the sensor 10 are a length of about 1.5 inches and a diameter of from about 0.25 to 0.375 inches. The body 12 can be of any suitable material, for example, an epoxy plastic, TEFLON, or stainless steel.

Sensor 10 is configured to be able to transmit a narrow beam of ultrasonic energy from the piezoelectric element through the air to be reflected from the surface of the air-liquid interface of a container that has previously been filled back to the element. Transmitting ultrasonic energy through air has the advantage of range resolution. The system achieves this advantage using high frequency transmission through air. That is, the sensor element is supplied signals for transmission in the range of from 1 to 2 Mhz. The velocity of sound in air at room temperature is 343.2 meters per second, and at a 2 Mhz ultrasonic frequency, a system resolution of 0.0003 inches can be achieved.

In the preferred embodiment of the invention, a 1 Mhz to 2 Mhz miniature ultrasonic sensor is used to measure accurately liquids in small containers. A 1–2 Mhz sensor can have a multi-layer matching impedance structure to match the sensor with air. Each layer of the matching impedance is designed to match a quarter wavelength to an adjacent layer until the final layer, which matches closely to air, provides a complex impedance match with the impedance of the air. This 1–2 Mhz sensor has a very narrow beam angle, of less than 2° (2 degrees), measurement resolution of +0.0005" and a dead zone of $\leq 0.5"$.

Figure 2:
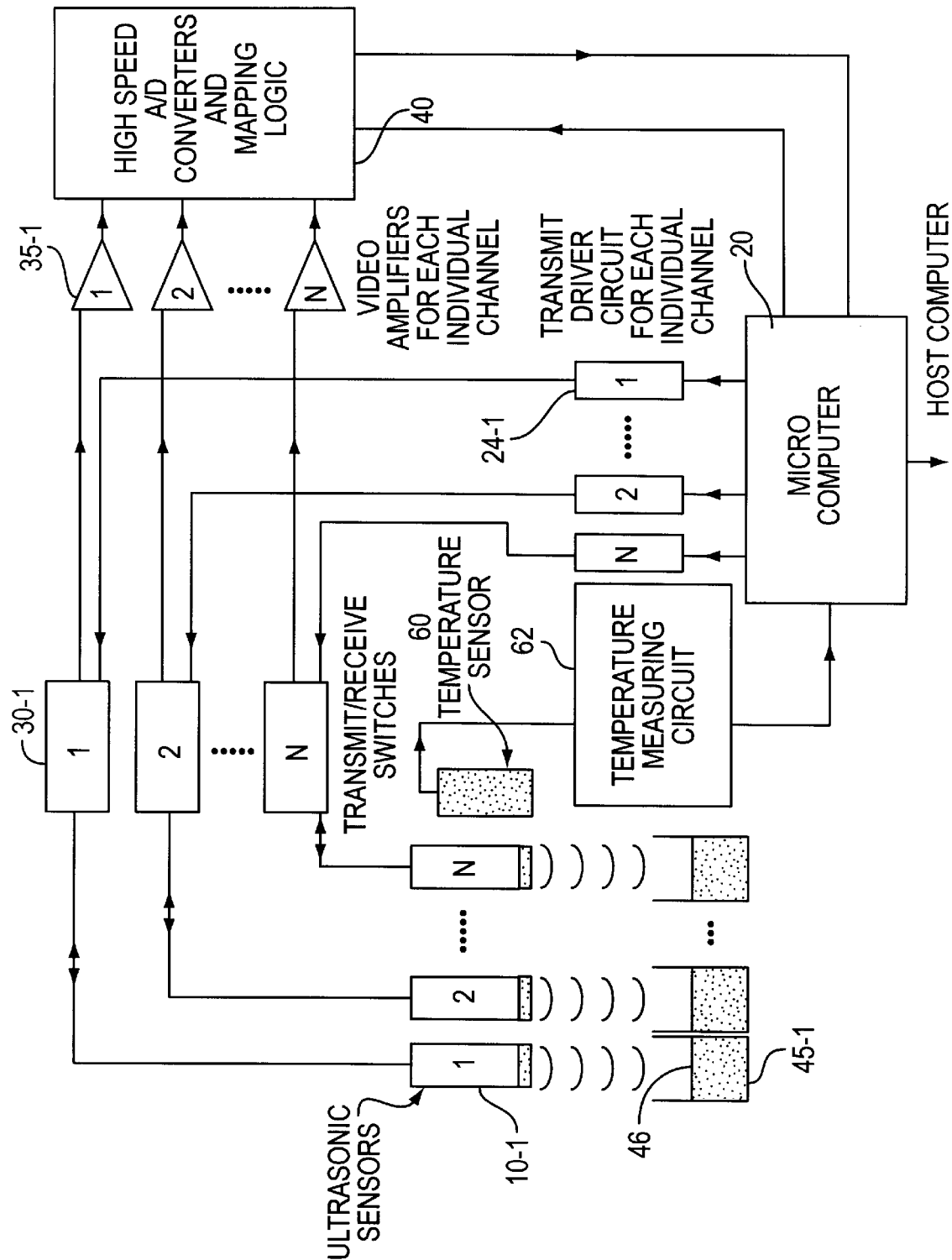
FIG. 2 is a schematic block diagram of the electronic circuit.

FIG. 2 is a block diagram for a single/multichannel system. There are a plurality of the sensors 10, designated 10-1, 10-2, . . . 10-N. A programmed/programmable microprocessor 20 is programmed to control operation of the system. The microprocessor 20 sequentially produces a drive signal of the desired frequency, such as 2 Mhz, for each of the sensors 10 which is applied to a respective driver circuit 24-1, 24-2, . . . 24-N. The drive signal produced by the microprocessor is a series, or burst, of rectangular pulses that is amplified by the respective driver circuit 24. For sequential actuation of the sensors, a time interval is provided between the drive signal to each sensor 10 to allow for reception of the signal reflected from the interface and processing of the acquired data.

A transmit/receive switch 30 is connected to each sensor 10. Each switch 30 has a connection to its respectively connected sensor 10 and also a connection to a respective amplifier 35, which is preferably of the wideband video type. The operation of each switch 30 is controlled by the microprocessor 20 so as to be open to convey the signal for transmission from its connected driver circuit 24 to its connected sensor 10. The microprocessor then closes the switch 30 in the transmission direction to the sensor 10 and opens the signal path from the sensor to the respectively connected amplifier 35. In the embodiment presently being described, only one switch 30 operates at a time, so that only one sensor at a time is operative.

FIG. 2 diagrammatically shows the plurality of sensors 10 arrayed in a row with the piezoelectric element end opposing the open (top) end of a respective container 45 that holds an amount of a liquid 46. The container has been filled prior to reaching the measuring station at the sensors. The internal dimensions of the container are stored in a memory which is either separate from or a part of the microprocessor. The term container is used in the broad sense and covers any type of vessel such as, for example, test tubes, vials, a well of a microplate that has been filled with liquid, etc. Each sensor 10 is at a fixed, and known, distance from the top end of its opposing container 45 and the beam of ultrasonic energy it produces is aimed into the open top of the opposing container. As explained below, in one embodiment of the invention, rows of the containers 45 are passed in a stepwise fashion below the row of sensors.

In one mode of operation of the system of FIG. 2, each sensor 10 of the row is operated in sequence. The actuated sensor is supplied a burst of the drive signals for transmission to its opposing container from microprocessor 20 after having been amplified by the sensor's respective driver circuit 24 through the switch 30, which is gated open by a command signal from the microprocessor. This time is marked, or stored, by the microprocessor as the beginning of a time measuring period. After the sensor transmits its signal, the microprocessor 20 sends a command signal to the switch 30 to open the transmission path from the sensor to its connected amplifier 35.

The activated sensor transmits a beam of energy into the open top of the opposing container to impinge on the top surface of the liquid, i.e., the air-liquid interface, and be reflected back to the sensor. The received reflected signal is applied from the output of amplifier 35 to the input of a high speed A/D converter and mapping logic circuit 40. Receipt of the signal by circuit 40 stops the time measurement and this is converted into digital data that is supplied to the microprocessor. The entire row of sensors 10-1 . . . 10-N is operated in sequence and the data produced in A/D converter 40 is applied to the microprocessor.

The round trip transit time of the energy from a sensor 10 to the air-liquid interface and back to the sensor is used as a factor in the measurement of the volume of liquid in a container. That is, if the height of the interior of the container 45 is known, measurement of the distance to the top surface of the liquid in the container to the sensor (minus the known distance of the sensor to the top of the container) determines the height of the liquid column in the container. Knowing this dimension and the inner diameter of the container, the volume can be calculated. The microprocessor 20 is programmed, for example, from a personal computer, to store the various factors, such as container height and inner diameter and distance from the top of the container to the sensor. The microprocessor 20 also receives temperature data from a temperature sensor 60 which is converted into digital format by the measuring circuit 62. Upon being provided with the time measurement (converted into digital format) and with the other data being stored, the microprocessor computes the volume of liquid in each of the containers and the computed result is stored.

In the overall operation of the system, the microprocessor triggers the production of bursts of pulses at an ultrasonic frequency in the range of 2 Mhz. The width of the pulses is from ten to fifteen microseconds. The pulses are applied to the sensor transducer where they are converted into pulses of ultrasonic energy which are radiated in a narrow beam through the air into the opposing container. In the intervals between the bursts of transmitted pulses, the ultrasonic energy is reflected form the container air-liquid interface back up to the transducer which converts the returned energy into signal pulses which are amplified. The signal pulses are A/D converted and digitized. The microprocessor measures the time difference between the transmission of the ultrasonic energy and its reflection from the air-liquid interface of the container.

The system also includes a temperature sensor that is applied to a temperature measuring circuit. The temperature data in digital form is also applied to the microprocessor which modifies the output date with corrected velocity of sound at that temperature. Since the position of the sensor and its transducer is known as well as the internal diameter of the test tubes, these parameters being programmable into the microprocessor, the volume of the liquid is calculated in the microprocessor.

A signature is produced for the row of containers measured by the row of sensors 10 and is mapped in memory, which can be located in the microprocessor. The microprocessor analyzes the data in real time and outputs the corresponding liquid volume and/or simply the presence/absence of liquid in the containers. The liquid volume measurement of the plurality of containers can be outputted to a suitable mechanism, such as one for marking containers that are not filled with the required volume, such as being empty, or can be stored in memory for further use.

The system can have the plurality of the sensors 10 all transmitting and receiving data simultaneously. For this to take place, each sensor would be under the control of its own microprocessor and a common storage used to map the results of the plurality of volume measurement results. For a single container system, response time can be as fast as two milliseconds with a one millisecond repetition rate.

Figure 3:
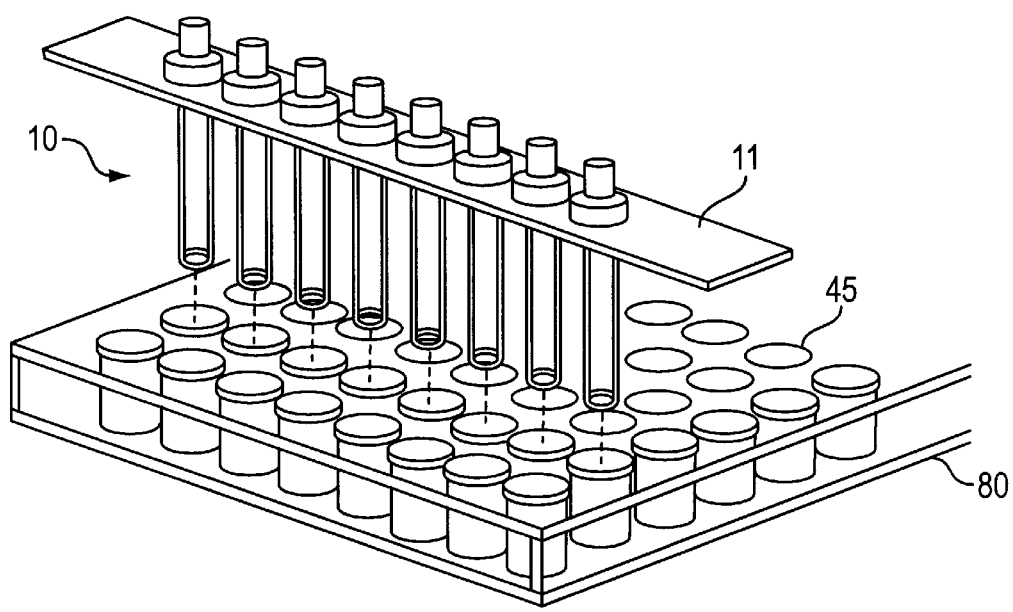
FIG. 3 is a perspective view of an arrangement for filling and measuring the liquid volume in a plurality of containers.

FIG. 3 shows a microplate 80 that is used to hold a plurality of containers 45. In a typical application, there are 12 rows of 8 containers, making a total of 96 containers held by the microplate. A bank of a row of eight sensors 10 are mounted on a common plate 11 and positioned above the microplate. The microplate and sensor bank are moved relative to each other by a suitable stepping mechanism on a row by row basis. That is, after the measuring system of FIG. 2 has completed making the measurements of the liquid volume of each of the containers 45 in one of the rows, either sequentially or simultaneously, a stepping signal is provided to position the next row of containers under the bank of sensors.

The volummetric measurement results for all of the containers of the microplate preferably are stored, or mapped, in memory. The containers 45 in the tray 80 can be of different shapes and volume so long as they are in an order and the dimensional data for the different containers has been previously appropriately programmed into the microprocessor. The map of the filling volume of the containers in the microplate can be displayed, such as by printing or on a monitor, for use by an operator.

A major advantage of the mapping and pattern recognition technique is that it eliminates a human interface. The system can work and stand alone. It may also be independent of microplates moment, irregular container shape and size, change in velocity of the carrying mechanism, etc.

FIGS. 4A, 4B and 4C show different forms of containers whose volummetric fill can be measured. As indicated above, the dimensions of the containers being measured are programmed into the microprocessor 20.

Figure 5:
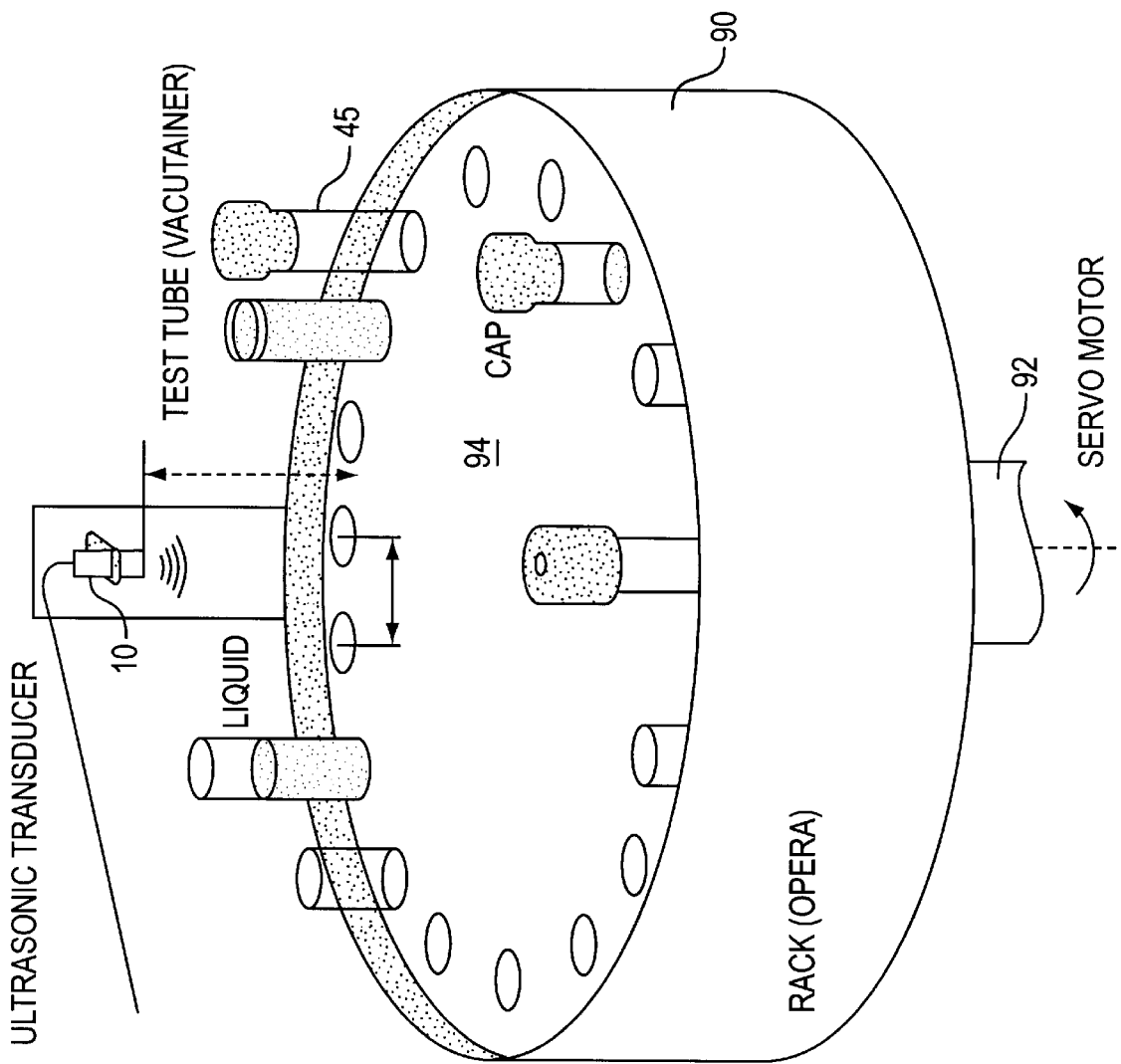
FIG. 5 is a view of a carousel arrangement for measuring the volume in sequence of each of a plurality of containers.

FIG. 5 shows another embodiment of the invention in which a plurality of containers 45 are placed in a tray 94 that is mounted in a carousel 90. The carousel is on a shaft 92 which is rotated by a servomotor that is linked to the microprocessor of FIG. 2. Here the volume of liquid in each of the containers on the tray is measured one at a time on a sequential basis. Only one of the sensors 10 of the system shown in FIG. 2 need be used. As the carousel is stepped, for example, every millisecond, the microprocessor 20 controls the system to transmit and receive ultrasonic energy though the electronic circuit as previously described. The containers on the tray 94 can be of different shapes and volume so long as they are in an order that has been previously programmed into the microprocessor with the dimensional data.

In a continuous operating mode for the system of FIG. 5, the carousel is stepped continuously and no external synchronizing signal is required and continuous data is gathered. In a strobe mode of operation, there is a wait for a valid "Tray Sync" pulse and "Well Strobe" to synchronize the measurement to outside events. The "Tray Sync" informs the unit that a new microplate or tray 94 placed in the carousel is to be processed. "Well Strobe" starts the ultrasonic measurement cycle to determine the volume in each of the containers.

The non-contact, non-invasive ultrasonic technology of the invention provides a fast response, very high resolution, high speed, no lead technique for measuring relatively small changes in volume in filling microwell plates, test tubes and vials.

The non-contact liquid level measurement using ultrasonic energy is an attractive alternative to contact type measurement systems. All problems of cross-contamination are averted since the liquid is never touched by the sensor. Processing speed is also increased since no movement is required to bring the liquid into contact with a sensor probe. The system is useful for such high speed automated processing with an accuracy of 0.001 inches. The system uses an ultrasonic transducer of less than 0.2 inches in diameter. Containers with narrower openings can be accessed by using a disposable collar.

Also, the two dimensional mapping technique with pattern recognition logic eliminates a major problem of synchronizing the measurement with a driving mechanism. Using a parallel flash technique, all of the ultrasonic sensors can transmit and receive signals simultaneously for processing.

The invention solves a problem of meeting sterility requirements as well as very special processing demands. The system satisfies a need for accurate and reliable sensors and associated instrumentation.

I claim:

1. A non-contact ultrasonic system for measuring the volume of liquid in a each of a plurality of containers, comprising:

an ultrasonic sensor disposed opposite the top of said containers;

a circuit for providing pulses of ultrasonic energy for transmission through the air to the air-liquid interface of liquid in each container and for measuring the round trip transit time from the sensor to the interface and back to the sensor;

a computer programmed with internal dimensional data of each container for computing the volume of liquid result in the container based on said data and the round trip transit time.

2. A system as in claim 1 and further comprising a memory for storing the measured volume result for each container.

3. A system as in claim 1 wherein there is a single sensor, and moving means for moving each of said plurality of containers relative to said single sensor for said single sensor to oppose the top of a said container to permit the round trip transit time measurement to be made for each said container.

4. A system as in claim 3 wherein the plurality of containers have different internal dimensions and said computer is programmed with dimensional data of the different containers and computes the volume of liquid result for each container based on said dimensional data corresponding to the container whose liquid volume is being measured and the round trip transit time of the ultrasonic energy transmitted to that container.

5. A system as in claim 4 further comprising a memory for storing the measured liquid volume result of each of said plurality of containers.

6. A system as in claim 3 further comprising a carousel for holding a tray in which said plurality of containers are held, and moving means for moving said carousel and the plurality of containers relative to said single sensor to successively measure the round trip transit time of the ultrasonic energy for each of the containers held in said tray.

7. A system as in claim 3 wherein there are a plurality of said sensors each to oppose the top of a respective container to permit the round trip transit time measurement to be made for each container opposing a sensor.

8. A system as in claim 7 further comprising a memory for storing the measured volume data for each of the plurality of containers.

9. A system as is claim 8 wherein each of said plurality of sensors is actuated in sequence to measure the round trip transit time of the ultrasonic energy from each said sensor to the air-liquid interface of the respective opposing container.

10. A system as is claim 8 wherein all of said plurality of sensors are actuated at substantially the same time to measure the round trip transit time of the ultrasonic energy from each said sensor to the air-liquid interface of the respective opposing container.

11. A system as in claim 8 wherein the plurality of containers have different internal dimensions and said computer is programmed with dimensional data of the different volume containers and computes the volume of liquid result for each container based on said dimensional data corresponding to the container whose liquid volume is being measured and the round trip transit time of the ultrasonic energy from the respective sensor transmitted to that container.

12. A system as in claim 7 further comprising a microplate for holding a plurality of containers in an array having a pattern to correspond to the arrangement of said plurality of sensors for measurement of the volumes of the plurality of containers in the array.

13. A system as in claim 12 wherein said microplate holds a plurality of said arrays of containers, and moving means for moving said microplate relative to said plurality of sensors to move each array of containers to oppose said plurality of sensors.

14. A system as in claim 1 wherein the frequency of the pulses of ultrasonic energy is at least 1 Mhz.

15. A system as in claim 1 wherein the beam angle of the energy transmitted is not greater than 2°.

16. A system as in claim 15 wherein the dead zone of signal response of the sensor is $\leq 0.5"$.

17. A non-contact ultrasonic system for measuring the volume of liquid in a container comprising:

a single ultrasonic sensor disposed opposite the top of said container;

a circuit for providing pulses of ultrasonic energy at a frequency of at least 1 Mhz for transmission through the air to the air-liquid interface of liquid in the container and for measuring the round trip transit time from said single the sensor to the interface and back to said single sensor; and a computer programmed with internal dimensional data of the container for computing the volume of liquid result in the container based on said data and the round trip transit time.

18. A system as in claim 17 wherein the beam angle of the energy transmitted is not greater than 2°.

19. A system as in claim 18 wherein the dead zone of signal response of the sensor is $\leq 0.5"$.

20. A non-contact ultrasonic system for measuring the volume of liquid in a container comprising:

an ultrasonic sensor disposed opposite the top of said container;

a circuit for providing pulses of ultrasonic energy at a frequency operating with said sensor for transmission of the ultrasonic energy from said sensor at a beam angle of not greater than 2°, the ultrasonic energy being transmitted through the air to the air-liquid interface of liquid in the container, and for measuring the round trip transit time from the sensor to the interface and back to the sensor; and a computer programmed with internal dimensional data of the container for computing the volume of liquid result in the container based on said data and the round trip transit time.

* * * * *